United States Patent [19]
Brink et al.

[11] Patent Number: 5,529,935
[45] Date of Patent: Jun. 25, 1996

[54] METHOD FOR DETERMINING ORGANOAMINES CONCENTRATIONS IN CHLOROSILANE

[75] Inventors: Robert G. Brink, St. Louis; David M. Muller; Guy L. Reggio, both of Midland, all of Mich.

[73] Assignee: Hemlock Semiconductor Corporation, Hemlock, Mich.

[21] Appl. No.: 442,614

[22] Filed: May 17, 1995

[51] Int. Cl.$^6$ .................................... G01N 30/12
[52] U.S. Cl. ........................... 436/111; 436/111
[58] Field of Search ..................... 436/106, 111, 436/112; 423/342, 240 R; 210/656, 702, 659, 698, 723, 795, 732

[56] References Cited

U.S. PATENT DOCUMENTS

| | | | |
|---|---|---|---|
| 3,928,542 | 12/1975 | Bakay | 423/342 |
| 3,968,199 | 7/1976 | Bakay | 423/347 |
| 4,113,845 | 9/1978 | Litteral | 423/342 |
| 4,242,097 | 12/1980 | Rich, Jr. et al. | |
| 4,255,348 | 5/1981 | Herdle et al. | 556/410 |
| 4,395,389 | 7/1983 | Seth | 523/341 |
| 4,548,917 | 10/1985 | Lepage et al. | 502/150 |
| 4,595,775 | 6/1986 | Arkles | 556/409 |
| 4,927,616 | 5/1990 | Marlett | 423/347 |
| 5,045,621 | 9/1991 | Suzuki | 528/14 |
| 5,118,485 | 7/1992 | Arvidson et al. | 423/342 |

OTHER PUBLICATIONS

Bernstein, On the Mechanism of Interaction between Tertiary Amines and Trichlorosilanes, J of Amer. Chem. Soc 1992, 3, 1970 pp. 699–700.

Benkeser et al. Evidence of the Existense of the Trichlorosilyl Anion, J of Amer. Chem. Soc. 1992, 3, 1970, pp. 697–698.

Bouyoucos, Analytical Chemistry 49:401–403, (1977).

Buechele et al., Anal. Chem. 54:2114–2115, (1982) pp. 2113–2114 Am.

Bouyoucos et al., Am. Ind. Hyg. Assoc. J. 44:119–122, (1983).

Gilbert et al., Anal. Chem. 56:106–109. (1984).

Daigle et al., Chromatographia 32:143–147, (1991).

Burg, J. Am. Chem. Soc. 76:2674–2675, (1954).

Ring et al., J. Am. Chem. Soc. 93:265–267, (1971).

Jeng et al., Inorg. Chem. 29:837–842, (1990).

*Primary Examiner*—Jill Warden
*Assistant Examiner*—Alexander Markoff
*Attorney, Agent, or Firm*—William F. Boley

[57] ABSTRACT

A process for determining the organoamines concentrations in chlorosilane. The process comprises separating a mixture comprising as a major portion a chlorosilane and as minor portion an organoamine having a boiling point less than or about the boiling point of the chlorosilane, where the organoamine is complexed in situ in the chlorosilane to form an organoamine complex which vaporizes at a temperature greater than the boiling point temperature of the chlorosilane, into a vapor phase comprising the chlorosilane and a solid phase comprising the organoamine complex. An aqueous solution of the solid phase is formed and analyzed by ion exchange chromatography for organoamine content. The present invention is particularly useful for analyzing chlorosilanes for dimethylamine and trimethylamine where the chlorosilane or residual hydrogen chloride in the chlorosilane serves to complex the organoamine.

11 Claims, No Drawings

METHOD FOR DETERMINING ORGANOAMINES CONCENTRATIONS IN CHLOROSILANE

BACKGROUND OF INVENTION

The present invention is a process for determining the organoamines concentrations in chlorosilane. The process comprises separating a mixture comprising as a major portion a chlorosilane and as a minor portion an organoamine having a boiling point less than or about the boiling point of the chlorosilane, where the organoamine is complexed in situ in the chlorosilane forming an organoamine complex which vaporizes at a temperature greater than the boiling point of the chlorosilane, into a vapor phase comprising the chlorosilane and a solid phase comprising the organoamine complex. An aqueous solution of the solid phase is formed and analyzed by ion exchange chromatography for organoamine content. The present invention is particularly useful for analyzing chlorosilanes for dimethylamine and trimethylamine where the chlorosilane or residual hydrogen chloride in the chlorosilane serves to complex the organoamine.

The production of semiconductor grade silicon typically involves the decomposition of a chlorosilane gas such as trichlorosilane to deposit silicon onto a heated element by a process referred to as chemical vapor deposition (CVD). Continuous improvement in the technology to concentrate integrated circuits on silicon wafers has created a continuing need to improve the purity of chlorosilane gas used in the deposition process. Organoamines represent a potential source of detrimental contaminates in chlorosilanes. Therefore, it is desirable to have a reliable method for measuring the levels of organoamines in chlorosilanes.

Typical commercial processes for manufacturing chlorosilanes involve the contact of hydrogen chloride with silicon metalloid in a fluidized-bed reactor. The product of this reaction is a mixture comprising chlorosilanes, including silane ($SiH_4$), chlorosilane, dichlorosilane, trichlorosilane, and tetrachlorosilane. In addition the mixture can contain hydrogen chloride. In certain incidences it can be desirable to disproportionate this mixture to increase the proportion of commercially more desirable chlorosilanes, such as trichlorosilane. In addition during conduct of the CVD process for making semi-conductor grade silicon, a gaseous product is produced comprising more reduced chlorosilanes, that is chlorosilanes having more hydrogen. It is often desirable to disproportionate more reduced chlorosilanes to more commercially desirable chlorosilanes such as trichlorosilane.

The disproportionation of chlorosilanes occurs slowly in the absence of a catalyst. However, in the presence of a catalyst such as an organoamine the disproportionation can occur readily. Preferred is when the organoamine is attached to a solid support. Examples of the use of supported organoamine catalyst in the disproportionation of chlorosilanes are described in Litteral, U.S. Pat. No. 4,113,845; Bakay, U.S. Pat. No. 3,968,199; Bakay, U.S. Pat. No. 3,928,542; Lepage et al., U.S. Pat. No. 4,548,917; and Seth, U.S. Pat. No. 4,395,389. Also, described in Arvidson, et al., U.S. Pat. No. 5,118,485, is a process where lower-boiling silanes comprising an effluent gas from a CVD process can be disproportionated in the presence of a nitrogen containing material on a solid support. The present invention is especially useful for analyzing the product of such disproportionation processes for organoamines resulting from the decomposition of the nitrogen containing catalysts.

The analysis of aqueous solutions by ion exchange chromatography (IEC) for organoamines has been described. For example, Bouyoucos, Analytical Chemistry 49:401–403, 1977, describes and IEC technique for analyzing an aqueous solution for determination of ammonia, monomethylamine, dimethylamine, and trimethylamine. Buechele et al., Anal. Chem. 54:2114–2115, 1982, describe a process for analyzing an aqueous solution for ethylenediamine by IEC. Bouyoucos et al., Am. Ind. Hyg. Assoc. J. 44:119–122, 1983, describe an IEC process for analyzing an aqueous solution for ammonia, monomethylamine, dimethylamine, and trimethylamine, where the amine was collected from air by adsorption on to silica gel. Gilbert et al., Anal. Chem. 56:106–109, 1984, report a process for IEC determination of morpholine and cyclohexylamine in aqueous solutions containing ammonia and hydrazine. Rich et al., U.S. Pat. No. 4,242,097, describe a method and apparatus for quantitative analysis of weakly ionized anions, such as organoamines, by IEC. Daigle et al., Chromatographia 32:143–147, 1991, describes a process for determining the concentration of various organoamines in an aqueous solution by IEC. Diagle et al. reported detection limits as low as tenths of parts per million (ppm) of the organoamines.

The ability of chlorosilanes to complex with trimethylamine at low temperatures is reported by Burg, J. Am. Chem. Soc. 76:2674–2675, 1954. Burg reports that the complex of tetramethylsilane with trimethylamine begins to dissociate at about −54.1° C., the complex of trichlorosilane with trimethylamine begins to dissociate at about −30° C., and the complex of dichlorosilane with trimethylamine may be stable at temperatures below about 38° C. Ring et al., J. Am. Chem. Soc. 93:265–267, 1971, reports the formation of a 1:1 adduct of trichlorosilane with trimethylamine by multiple condensations procedures at a temperature of −78° C. The salt $HN(CH_3)_3^+SiCl_3^-$ was reported to be thermally stable with evidence of some decomposition at 38° C. Jeng et al., Inorg. Chem. 29:837–842, 1990, report a matrix isolation technique and twin-jet deposition method to isolate and characterize the reaction products of the codeposition of trichlorosilane with bases containing nitrogen. Jeng et al. conclude that the codeposition of the tested bases containing nitrogen with trichlorosilane led to the formation of isolated 1:1 molecular complexes. Jeng et al., concluded that the base interacted with the silicon center on trichlorosilane to form a coordinated complex.

The problem to be solved by the present method is how to analyze a chlorosilane for organoamine contaminants, where at least one of the organoamines has a boiling point less than or about the boiling point of the chlorosilane and the chlorosilane may contain organoamine complexes capable of sublimation and subsequents condensing causing fowling of analytical devices.

The ability to analyze the concentration of organoamines in chlorosilanes is complicated by the reactivity of chlorosilanes. Chlorosilanes hydrolyze on contact with water, therefore techniques such as ion exchange chromatography using an aqueous carrier will not work. In addition when subject to high heat such as in atomic emission or atomic adsorption, the chlorosilane decompose into particulate silica. In general techniques such as infrared adsorption and gas chromatography fail because complexes of the organoamine collect in the equipment making the results unreliable.

Unexpectly, the present inventors have found that organoamines having a boiling point less than or about the boiling point of the chlorosilane to be analyzed can readily complex with a Lewis acid. The resulting organoamine and Lewis acid complex have sufficient stability to allow the chlorosilane to be evaporated leaving a residue comprising the complexed organoamine. An aqueous solution of the residue comprising the complexed organoamine can then be formed and analyzed for organoamine content by ion exchange chromatography.

SUMMARY OF INVENTION

The present invention is a process for determining the organoamines concentrations in chlorosilane. The process comprises separating a mixture comprising as a major portion a chlorosilane and as minor portion an organoamine having a boiling point less than or about the boiling point of the chlorosilane, where the organoamine is complexed in situ in the chlorosilane to form an organoamine complex which vaporizes at a temperature greater than the boiling point of the chlorosilane, into a vapor phase comprising the chlorosilane and a solid phase comprising the organoamine complex. An aqueous solution of the solid phase is formed and analyzed by ion exchange chromatography for organoamine content. The present invention is particularly useful for analyzing chlorosilanes for dimethylamine and trimethylamine where the chlorosilane or residual hydrogen chloride in the chlorosilane serves to complex the organoamine.

DESCRIPTION OF INVENTION

The present invention is a method for determining organoamine contaminants concentrations in chlorosilane. The method comprises:

(A) separating a mixture comprising as a major portion a chlorosilane described by formula $$Cl_nSiH_{4-n},\qquad(1)$$

where n=2, 3, or 4, and as a minor portion an organoamine having a boiling point less than or about the boiling point of the chlorosilane, where the organoamine is complexed in situ in the chlorosilane forming an organoamine complex which vaporizes at a temperature higher than the boiling point temperature of the chlorosilane, into a vapor phase comprising the chlorosilane and a solid phase comprising the organoamine complex, (B) forming an aqueous solution of the solid phase comprising the organoamine complex, and (C) analyzing the aqueous solution for organoamine content by ion exchange chromatography.

The chlorosilane which can be analyzed by the present method is described by formula (1). The chlorosilane can be dichlorosilane, trichlorosilane, tetrachlorosilane, or a mixture of two or more of the described chlorosilanes. A preferred chlorosilane is one comprising as a major portion trichlorosilane. Even more preferred is a distillate comprising as a major portion trichlorosilane, where the distillate is a distillation product of a chlorosilane mixture which has been disproportionated in the presence of an amine catalyst. Such disproportionation processes are described in, for example, Litteral, U.S. Pat. No. 4,113,845 and Arvidson, U.S. Pat. No. 5,118,485 which are incorporated by reference.

In mixture with the chlorosilane is a minor portion of an organoamine having a boiling point less than or about the boiling point of the chlorosilane. By the term "minor portion" it is meant that the organoamine is present in the chlorosilane at a level that would normally be considered a contaminant. However, the concentration of the organoamine in the chlorosilane is not critical to the present invention and with appropriate dilution or concentration procedures the organoamine can be detected within a wide concentration range. The present method is especially useful for measuring organoamine concentration in the chlorosilane in the parts per million (ppm) and lower range.

The organoamine has a boiling point less than or about the boiling point of the chlorosilane. The use of the term "about" in this context means that the organoamine has a boiling point similar enough to that of the chlorosilane that one of ordinary skill in the art would consider it difficult to separate the two compounds by methods exploiting differences in boiling temperatures. Generally, it is preferred that the organoamine have a boiling point within a range of less than the boiling point of the chlorosilane to 10° C. greater than the boiling point of the chlorosilane.

The organoamine is complexed in situ in the chlorosilane forming an organoamine complex which vaporizes at a temperature higher than the boiling point temperature of the chlorosilane. Unexpectly, the present inventors have found that organoamines having boiling points less than or about the boiling point of the chlorosilane do not vaporize along with the chlorosilanes at the boiling point of the chlorosilane. This discovery allows separation of a mixture comprising chlorosilane and a minor portion of an organoamine into a vapor phase comprising the chlorosilane and a solid phase comprising the organoamine. An aqueous solution comprising the solid phase can then be made and analyzed by ion exchange chromatography to determine organoamine content. The present inventors believe that the reason the described separation can be effected is that the organoamine when present in the chlorosilane forms a complex with other materials present in the mixture to form a higher boiling complex. The type compound complexing with the organoamine is not critical to the present invention and can be any material capable of forming a complex with an organoamine contaminant in chlorosilane, where the complex has a temperature of vaporization sufficient to allow separation from the chlorosilane by vaporization of the chlorosilane.

The higher boiling complex may be a complex of the organoamine with a Lewis acid. The inventors believe that at least a portion of the Lewis acid complexing with the organoamine may be chlorosilane. The Lewis acid may be hydrogen chloride. The hydrogen chloride can be residual hydrogen chloride typically present in the chlorosilane or hydrogen chloride may be added to the chlorosilane.

Vaporization of the chlorosilane can be effected by standard procedures for vaporizing liquids. It is preferred that the vaporization of the chlorosilane be effected under anhydrous conditions, since chlorosilanes can hydrolyze to form gels when contacted with water. Vaporization of the chlorosilane can be effected by use of elevated temperature, reduced pressure, or a combination of elevated temperature and reduced pressure, combined with a method to remove the chlorosilane vapor as it is formed. Vaporization of the chlorosilane can be effected by contacting a flowing inert gas such as nitrogen, argon, or helium with the chlorosilane. In a preferred process vaporization of the chlorosilane is effected by contacting a flowing Lewis acid gas with the chlorosilane. A preferred Lewis acid gas is anhydrous hydrogen chloride. The anhydrous hydrogen chloride gas may be diluted in an inert gas such as nitrogen.

After the mixture is separated into the vapor phase comprising the chlorosilane and the solid phase comprising the organoamine complex, an aqueous solution of the solid phase is formed. The inventors do not wish to be limited to the requirement that a true aqueous solution of the solid phase be formed. The inventors intend the term "aqueous solution" to include all conditions in which organoamine in the solid phase is recovered in aqueous media in a manner allowing the aqueous media to be analyzed by ion exchange chromatography for organoamines. The amount of water used to form the aqueous solution is not critical to the present invention and will be determined by the amount of organoamine present in the solid phase and the detection range of the detector used to analyze the eluent from the ion exchange chromatograph.

The aqueous solution of the solid phase is analyzed by ion exchange chromatography for organoamine content. The method for conducting the ion exchange chromatography is not critical to the present invention and can be any of those known in the art for analyzing aqueous solutions for organoamines by ion exchange chromatography. A method for analyzing an aqueous solution for organoamine is provided in the examples herein. Also, an ion exchange chromatography method useful in the present process is described, for example, in Daigle et al., Chromatographia 32:143–147, 1991.

The following examples are provided to illustrate the present invention. The examples are not intended to limit the scope of the present claims.

EXAMPLE 1

A mixture comprising 22 part per million (ppm) of trimethylamine (TMA) in trichlorosilane (TCS) was formed in a stainless steel cylinder. The mixture was transferred to a teflon drying vessel in three separate aliquots. The first aliquot was evaporated to dryness by passing dried nitrogen gas across the top of the aliquot at room temperature. The second aliquot was evaporated to dryness by passing a mixture of anhydrous hydrogen chloride gas and nitrogen across the top of the aliquot at room temperature. The third aliquot was treated by pressuring the stainless steel cylinder with hydrogen chloride gas for several minutes at room temperature. Then the hydrogen chloride treated TMA in TCS mixture was transferred to a teflon drying vessel. This aliquot was evaporated to dryness by passing dried nitrogen gas across the top of the aliquot at room temperature. After each aliquot was evaporated to dryness, about 25 ml of deionized water was added to the teflon drying vessel to solubilize the resulting residue. The deionized water containing the solubilized residue was analyzed by ion-exchange chromatography. The analysis was conducted on a Dionex 2120 ion chromatograph (Dionex Corporation, Westmont, Ill.) using a CS10 chromatographic column, a CG10 guard column (sulfonated polystyrene cation beads) CMMS suppressor column using tetrabutyl ammonium hydroxide as the chemical regenerant, and a conductivity detector (IEC-CD). The column eluent was a mixture comprising 40 millimolar HCl and 4 millimolar diaminopropionic acid. The concentration of the trimethylamine ion was determined in the water solutions and are presented in Table 1 as a percent of the theoretical amount of TMA in each aliquot. The stainless steel cylinder in which the mixture comprising TMA and TCS was made was then washed with two aliquots of about 20 ml of deionized water. These washes were also analyzed for TMA by IEC-CD and the results are reported in Table 1 as a percent of TMA originally present in the stainless steel cylinder.

TABLE 1

| TMA Concentration Determination in TCS | | |
|---|---|---|
| | % TMA Recovered | % Total |
| Aliquot 1 | 15 | 5.3 |
| Aliquot 2 | 34 | 7.4 |
| Aliquot 3 | 10 | 4.2 |
| Wash 1 | 76 | 76.0 |
| Wash 2 | 7 | 7.1 |

The result indicate that essentially 100 percent of the TMA added to the TCS can be recovered in aqueous solution. It appears that the TMA is rapidly complexed in trichlorosilane to a non-volatile water soluble form, a significant portion of which may be retained in the mixing chamber and must be removed by washing with water.

EXAMPLE 2

Mixtures comprising TMA in TCS were formed in a stainless steel cylinder. The concentration of TMA in each mixture is reported in Table 2 under the heading "ppm TMA". Each mixture was transferred to a teflon drying vessel and evaporated to dryness by passing a dried gas across the mixture. For mixture 1, the dried gas was nitrogen. For mixture 2, the dried gas was a mixture of nitrogen with about 10 volume percent hydrogen chloride. For mixture 3, the stainless steel cylinder containing the TMA in TCS mixture was pressurized with anhydrous hydrogen chloride and the resulting mixture transferred to a teflon drying vessel. This mixture was evaporated to dryness by use of dried nitrogen. The residue from each of the mixtures was solubilized in deionized water and analyzed by IEC-CD as described in Example 1. In addition, the stainless steel cylinder in which the mixture was formed was washed with an aliquot of water and the water analyzed by IEC-CD. The results of the analysis are reported in Table 2. Results are reported as a percent of the TMA added to the stainless steel cylinder.

TABLE 2

| TMA Concentration Determination in TCS | | |
|---|---|---|
| | ppm TMA | % TMA Recovery |
| Mixture 1 ($N_2$ evaporation) | 22 | 64 |
| Mixture 1 wash | — | 23 |
| Mixture 2 ($N_2$/10% HCl evaporation) | 22 | 81 |
| Mixture 2 wash | — | 17 |
| Mixture 3 (HCl addition/$N_2$ evaporation) | 22 | 46 |
| Mixture 3 wash | — | 59 |

EXAMPLE 3

Mixtures comprising TMA in TCS were formed in a teflon cylinder. The concentration of TMA in each mixture is reported in Table 3 under the heading "ppm TMA". Each mixture was transferred to a teflon drying vessel and evaporated to dryness by passing a dried gas across the mixture. For mixture, 1, the dried gas was nitrogen. For mixture 2, the dried gas was a mixture of nitrogen with about 10 volume percent hydrogen chloride. For mixture 3, the teflon cylinder containing the TMA in TCS was pressurized with anhydrous hydrogen chloride. This mixture was then transferred to a teflon drying vessel and evaporated to dryness by use of dried nitrogen. All three mixtures were evaporated to dryness at room temperature. The residue from each of the mixtures was solubilized in deionized water and analyzed by IEC-CD as described in Example 1. In addition, the teflon cylinder in which the mixture was formed was washed with an aliquot of water and the water analyzed by IEC-CD for organoamine content. The results of the analysis are reported in Table 3 as a percent of the TMA added to the teflon cylinder.

TABLE 3

TMA Concentration Determination in TCS

|  | ppm TMA | % TMA Recovery |
|---|---|---|
| Mixture 1 ($N_2$ evaporation) | 42 | 33 |
| Mixture 1 wash | — | 2 |
| Mixture 2 ($N_2$/10% HCl evaporation) | 42 | 84 |
| Mixture 2 wash | — | 3 |
| Mixture 3 (HCl addition/$N_2$ evaporation) | 42 | 71 |
| Mixture 3 wash | — | 13 |

EXAMPLE 4

Mixtures comprising TMA in TCS were formed in a teflon cylinder. The concentration of TMA in each mixture is reported in Table 4 under the heading "ppm TMA". Each mixture was transferred to a teflon drying vessel and evaporated to dryness by passing a dried gas across the mixture at room temperature. For mixture 1, the dried gas was nitrogen. For mixture 2, the dried gas was a mixture of nitrogen with 10 volume percent hydrogen chloride. For mixture 3, the teflon cylinder containing the TMA in TCS mixture was pressurized with anhydrous hydrogen chloride. The mixture was then transferred to a teflon drying dish and evaporated to dryness by use of dried nitrogen. The residue from each of the mixtures was solubilized in deionized water and analyzed by IEC-CD as described in Example 1. In addition, the teflon cylinder in which the mixture was formed was washed with an aliquot of deionized water and the water analyzed by IEC-CD for organoamine content. The results of the analysis are reported in Table 4 as a percent of the TMA added to the teflon cylinder.

TABLE 4

TMA Concentration Determination in TCS

|  | ppm TMA | % TMA Recovery |
|---|---|---|
| Mixture 1 ($N_2$ evaporation) | 23 | 72 |
| Mixture 1 wash | — | 5 |
| Mixture 2 ($N_2$/10% HCl evaporation) | 23 | 45 |
| Mixture 2 wash | — | 33 |
| Mixture 3 (HCl addition/$N_2$ evaporation) | 23 | 67 |
| Mixture 3 wash | — | 12 |

EXAMPLE 5

A 420 g sample of a chlorosilane mixture comprising by weight about 95% tetrachlorosilane, 4% trichlorosilane and less than about 1% dichlorosilane, was placed in a teflon beaker. The chlorosilane mixture was evaporated to dryness by passing dry nitrogen gas over the mixture at room temperature. The solid remaining in the teflon flask were solubilized in 20 ml of deionized water. The resulting aqueous solution was analyzed by IEC-CD as described in Example 1. The chlorosilane mixture was determined to have by weight 42 ppb (parts per billion) trimethylamine, 448 ppb ammonium, and 46 ppb dimethylamine.

We claim:

1. A method for determining organoamine contaminants concentrations in chlorosilane, the method comprising:

(A) separating a mixture comprising as a major portion a chlorosilane described by formula $$Cl_nSiH_{4-n},$$

where n=2, 3, or 4, and as a minor portion an organoamine having a boiling point less than or about the boiling point of the chlorosilane, where the organoamine has been complexed in situ in the chlorosilane forming an organoamine complex which vaporizes at a temperature higher than the boiling point temperature of the chlorosilane, into a vapor phase comprising the chlorosilane and a solid phase comprising the organoamine complex, (B) forming an aqueous solution of the solid phase comprising the organoamine complex, and (C) analyzing the aqueous solution for organoamine content by ion exchange chromatography.

2. A method according to claim 1, where the organoamine has been complexed in situ in the chlorosilane with a Lewis acid.

3. A method according to claim 2, where the Lewis acid is selected from a group consisting of chlorosilane and hydrogen chloride.

4. A method according to claim 2, where the Lewis acid is selected from a group consisting of hydrogen chloride, trichlorosilane, and dichlorosilane.

5. A method according to claim 2, where the Lewis acid is hydrogen chloride.

6. A method according to claim 1, where the organoamine is selected from a group consisting of dimethylamine and trimethylamine.

7. A method according to claim 1, where the mixture comprising the chlorosilane is a distillation product of a chlorosilane mixture which has been disproportionated in the presence of an amine catalyst.

8. A method according to claim 1, where the organoamine has a boiling point within a range of less than the boiling point of the chlorosilane to 10° C. greater than the boiling point of the chlorosilane.

9. A method according to claim 1, where separating the mixture is effected by vaporization of the chlorosilane with a flowing Lewis acid gas.

10. A method according to claim 9 where the Lewis acid gas is anhydrous hydrogen chloride.

11. A method according to claim 1, where the chlorosilane is trichlorosilane, the organoamine is selected from a group consisting of dimethylamine and trimethylamine, and the organoamine has been complexed in situ in the chlorosilane with a compound selected from a group consisting of hydrogen chloride and trichlorosilane.

* * * * *